United States Patent
McCormack et al.

(10) Patent No.: US 6,238,767 B1
(45) Date of Patent: May 29, 2001

(54) LAMINATE HAVING IMPROVED BARRIER PROPERTIES

(75) Inventors: Ann Louise McCormack, Cumming; William Bela Haffner, Kennesaw, both of GA (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 0 days.

(21) Appl. No.: 09/127,705

(22) Filed: Jul. 31, 1998

Related U.S. Application Data (63) Continuation-in-part of application No. 08/929,432, filed on Sep. 15, 1997, now Pat. No. 5,997,981.

(51) Int. Cl.$^7$ ........................................................ B32B 5/16
(52) U.S. Cl. ............................ 428/99; 428/100; 428/516; 442/394; 604/370; 604/380; 604/384
(58) Field of Search ........................... 428/99, 100, 516; 442/394; 604/370, 384, 380

(56) References Cited

U.S. PATENT DOCUMENTS

| D. 7,178 | 2/1874 | Campbell | D5/58 |
|---|---|---|---|
| D. 43,596 | 2/1913 | Foster | D5/58 |
| D. 81,838 | 8/1930 | Maurus | D5/59 |
| D. 99,990 | 6/1936 | Brezner | D5/57 |
| D. 101,310 | 9/1936 | Lehmann | D5/59 |

(List continued on next page.)

FOREIGN PATENT DOCUMENTS

| 34 03 258 | 8/1985 | (DE) . |
|---|---|---|
| 35 20 630 | 12/1986 | (DE) . |
| 0247897 | 12/1987 | (EP) . |
| 0329377 | 8/1989 | (EP) . |
| 0456044 | 11/1991 | (EP) . |
| 0 712 892 | 5/1996 | (EP) . |
| 86 03164 | 6/1986 | (WO) . |
| 91/17296 | 11/1991 | (WO) . |
| 92/20251 | 11/1992 | (WO) . |
| 95/27005 | 10/1995 | (WO) . |

(List continued on next page.)

OTHER PUBLICATIONS

Case No. 13257, patent application entitled "Breathable Filled Film Laminate" filed Sep. 15, 1997.
Case No. 13324, patent application entitled "Nonwoven Bonding Patterns Producing Fabrics with Improved Strength and Abrasion Resistance" filed Sep. 15, 1997.
Serial No. 773,826 patent application filed Dec. 27, 1996 entitled "Stable and Breathable Films of Improved Toughness and Method of Making the Same." This was abandoned on Aug. 11, 1997 replaced by Serial No. 08/853,025 filed May 8, 1997, same title.
Exxon PE Grades, May 1996 (chart).
"New LLDPEs Offer Combined Properties, Processing Edge", Plastics World, Apr. 1997, p. 8.

(List continued on next page.)

Primary Examiner—Nasser Ahmad
(74) Attorney, Agent, or Firm—William D. Herrick (57) ABSTRACT

A composite material adapted for barrier garment applications is made by laminating a film with an amorphous polymer layer to a prebonded nonwoven web under conditions producing laminate bonds corresponding to the prebond locations, and unbonded areas between the bonds while maintaining constant film thickness. The composite has enhanced resistance to viral penetration for use as a surgical gown material, for example, and also desirably has a MVTR of at least about 300 g/m$^2$/24 hours and a hydrohead of at least about 50 mbar. In use as a component of a protective apparel such as a surgical gown or drape, the composite provides comfort and protection with reduced risk of film damage.

24 Claims, 5 Drawing Sheets

U.S. PATENT DOCUMENTS

| | | | |
|---|---|---|---|
| D. 102,691 | 1/1937 | Levy | D5/59 |
| D. 104,266 | 4/1937 | Jaeger | D5/59 |
| D. 154,162 | 6/1949 | Ryan | D18/2 |
| D. 188,408 | 7/1960 | Siegmann | D87/3 |
| D. 239,566 | 4/1976 | Vogt | D59/2 R |
| D. 298,701 | 11/1988 | Drew | D5/53 |
| D. 298,702 | 11/1988 | Drew | D5/53 |
| D. 356,688 | 3/1995 | Uitenbroek et al. | D5/52 |
| 3,338,992 | 8/1967 | Kinney | 264/24 |
| 3,341,394 | 9/1967 | Kinney | 161/72 |
| 3,502,763 | 3/1970 | Hartmann | 264/210 |
| 3,542,615 | 11/1970 | Dobo et al. | 156/181 |
| 3,645,992 | 2/1972 | Elston | 260/80.78 |
| 3,692,618 | 9/1972 | Dorschner et al. | 161/72 |
| 3,802,817 | 4/1974 | Matsuki et al. | 425/66 |
| 3,849,241 | 11/1974 | Butin et al. | 161/169 |
| 3,855,046 | 12/1974 | Hansen et al. | 161/150 |
| 3,894,904 | 7/1975 | Cook | 156/229 |
| 3,949,127 | 4/1976 | Ostermeier et al. | 428/137 |
| 4,048,364 | 9/1977 | Harding et al. | 428/113 |
| 4,100,324 | 7/1978 | Anderson et al. | 428/288 |
| 4,135,021 | 1/1979 | Patchell et al. | 428/134 |
| 4,147,827 | 4/1979 | Breidt, Jr. et al. | 428/218 |
| 4,154,885 | 5/1979 | Tecl et al. | 428/198 |
| 4,187,343 | 2/1980 | Akiyama et al. | 428/288 |
| 4,190,624 | 2/1980 | Alard et al. | 264/146 |
| 4,194,041 | 3/1980 | Gore et al. | 428/315 |
| 4,197,150 | 4/1980 | Breidt, Jr. et al. | 156/154 |
| 4,252,851 | 2/1981 | Lansbury et al. | 428/336 |
| 4,265,954 | 5/1981 | Romanek | 428/85 |
| 4,276,330 | 6/1981 | Stanley | 428/35 |
| 4,276,336 | 6/1981 | Sabee | 428/132 |
| 4,289,832 | 9/1981 | Schwarz | 428/542 |
| 4,297,408 | 10/1981 | Stead et al. | 428/240 |
| 4,303,708 | 12/1981 | Gebhardt et al. | 428/35 |
| 4,306,559 | 12/1981 | Nishizawa et al. | 128/287 |
| 4,312,964 | 1/1982 | Sekine et al. | 525/88 |
| 4,340,563 | 7/1982 | Appel et al. | 264/518 |
| 4,341,216 | 7/1982 | Obenour | 128/287 |
| 4,343,848 | 8/1982 | Leonard, Jr. | 428/156 |
| 4,344,999 | 8/1982 | Gohlke | 428/212 |
| 4,347,844 | 9/1982 | Ohki et al. | 128/287 |
| 4,350,655 | 9/1982 | Hoge | 264/145 |
| 4,352,849 | 10/1982 | Mueller | 428/213 |
| 4,364,985 | 12/1982 | Tokuyama et al. | 428/149 |
| 4,376,147 | 3/1983 | Byrne et al. | 428/167 |
| 4,377,616 | 3/1983 | Ashcraft et al. | 428/213 |
| 4,379,192 | 4/1983 | Wahlquist et al. | 428/156 |
| 4,384,024 | 5/1983 | Mitchell et al. | 428/349 |
| 4,386,129 | 5/1983 | Jacoby | 428/215 |
| 4,390,385 | 6/1983 | Ferguson et al. | 156/229 |
| 4,407,986 | 10/1983 | Nomura et al. | 523/200 |
| 4,430,468 | 2/1984 | Schumacher | 524/109 |
| 4,434,258 | 2/1984 | Schumacher et al. | 524/13 |
| 4,438,175 | 3/1984 | Ashcraft et al. | 428/315.5 |
| 4,439,478 | 3/1984 | Ferguson et al. | 428/137 |
| 4,443,511 | 4/1984 | Worden et al. | 428/198 |
| 4,443,513 | 4/1984 | Meitner et al. | 422/195 |
| 4,472,328 | 9/1984 | Sugimoto et al. | 264/41 |
| 4,525,407 | 6/1985 | Ness | 428/138 |
| 4,546,029 | 10/1985 | Cancio et al. | 428/141 |
| 4,573,991 | 3/1986 | Pieniak et al. | 604/385 A |
| 4,582,752 | 4/1986 | Ducan | 428/317.9 |
| 4,582,753 | 4/1986 | Duncan | 428/317.9 |
| 4,585,604 | 4/1986 | Okuyama et al. | 264/41 |
| 4,588,630 | 5/1986 | Shimalla | 428/131 |
| 4,595,629 | 6/1986 | Mays | 428/286 |
| 4,600,618 | 7/1986 | Raychok, Jr. et al. | 428/92 |
| 4,603,174 | 7/1986 | Okada et al. | 525/240 |
| 4,606,970 | 8/1986 | Sharps, Jr. | 428/301 |
| 4,613,643 | 9/1986 | Nakamura et al. | 524/426 |
| 4,672,091 | 6/1987 | Berta | 525/88 |
| 4,681,578 | 7/1987 | Anderson et al. | 604/385 |
| 4,681,793 | 7/1987 | Linman et al. | 428/138 |
| 4,684,568 | 8/1987 | Lou | 428/265 |
| 4,686,257 | 8/1987 | Mitsuno et al. | 524/449 |
| 4,698,372 | 10/1987 | Moss | 521/145 |
| 4,699,733 | 10/1987 | Matsumura et al. | 282/521 |
| 4,702,954 | 10/1987 | Duncan | 428/213 |
| 4,704,238 | 11/1987 | Okuyama et al. | 264/41 |
| 4,704,323 | 11/1987 | Duncan et al. | 428/286 |
| 4,705,813 | 11/1987 | Ito et al. | 521/92 |
| 4,734,324 | 3/1988 | Hill | 428/317.3 |
| 4,748,070 | 5/1988 | Beehler | 428/198 |
| 4,758,396 | 7/1988 | Crass et al. | 264/145 |
| 4,758,462 | 7/1988 | Park et al. | 428/213 |
| 4,761,318 | 8/1988 | Ott et al. | 428/85 |
| 4,761,324 | 8/1988 | Rautenberg et al. | 428/198 |
| 4,777,073 | 10/1988 | Sheth | 428/155 |
| 4,780,364 | 10/1988 | Wade et al. | 428/315.5 |
| 4,789,699 | 12/1988 | Kieffer et al. | 524/271 |
| 4,791,144 | 12/1988 | Nagou et al. | 521/90 |
| 4,814,124 | 3/1989 | Aoyama et al. | 264/41 |
| 4,818,464 | 4/1989 | Lau | 264/510 |
| 4,824,718 | 4/1989 | Hwang | 428/284 |
| 4,832,886 | 5/1989 | Douglas | 264/41 |
| 4,842,741 | 6/1989 | Coughlin et al. | 210/500.36 |
| 4,857,370 | 8/1989 | Overbergh et al. | 422/34.9 |
| 4,861,652 | 8/1989 | Lippert et al. | 428/284 |
| 4,863,792 | 9/1989 | Mrozinski | 428/315.5 |
| 4,867,150 | 9/1989 | Gilbert | 128/155 |
| 4,879,078 | 11/1989 | Antoon, Jr. | 264/41 |
| 4,902,553 | 2/1990 | Hwang et al. | 428/156 |
| 4,908,251 | 3/1990 | Iimura et al. | 428/68 |
| 4,909,971 | 3/1990 | Coughlin et al. | 264/45.5 |
| 4,910,639 | 3/1990 | Schloegl et al. | 361/323 |
| 4,921,652 | 5/1990 | Tsuji et al. | 264/41 |
| 4,921,653 | 5/1990 | Aoyama et al. | 264/41 |
| 4,923,650 | 5/1990 | Antoon, Jr. et al. | 264/41 |
| 4,929,303 | 5/1990 | Sheth | 156/209 |
| 4,960,637 | 10/1990 | Biczenczuk | 428/314.4 |
| 4,965,122 | 10/1990 | Morman | 428/225 |
| 4,965,123 | 10/1990 | Swan et al. | 428/314.4 |
| 4,981,747 | 1/1991 | Morman | 428/198 |
| 5,006,394 | 4/1991 | Baird | 428/138 |
| 5,008,296 | 4/1991 | Antoon, Jr. et al. | 521/91 |
| 5,026,591 | 6/1991 | Henn et al. | 428/198 |
| 5,026,592 | 6/1991 | Janocha et al. | 428/204 |
| 5,032,122 | 7/1991 | Noel et al. | 604/391 |
| 5,032,450 | 7/1991 | Rechlicz et al. | 428/196 |
| 5,073,316 | 12/1991 | Bizen et al. | 264/22 |
| 5,091,236 | 2/1992 | Keller et al. | 428/213 |
| 5,108,827 | 4/1992 | Gessner | 428/219 |
| 5,110,677 | 5/1992 | Barmore et al. | 428/349 |
| 5,114,781 | 5/1992 | Morman | 428/198 |
| 5,126,197 | 6/1992 | Schinkel et al. | 428/349 |
| 5,126,198 | 6/1992 | Schinkel et al. | 428/349 |
| 5,143,679 | 9/1992 | Weber et al. | 264/288.8 |
| 5,149,332 | 9/1992 | Walton et al. | 604/358 |
| 5,169,712 | 12/1992 | Tapp | 428/315.5 |
| 5,173,235 | 12/1992 | Kamei et al. | 264/154 |
| 5,176,953 | 1/1993 | Jacoby et al. | 428/315.5 |
| 5,204,179 | 4/1993 | Baker et al. | 428/336 |
| 5,208,098 | 5/1993 | Stover | 428/284 |
| 5,209,884 | 5/1993 | Wood, Jr. | 264/41 |
| 5,212,009 | 5/1993 | Peiffer et al. | 428/220 |
| 5,212,246 | 5/1993 | Ogale | 525/240 |
| 5,218,036 | 6/1993 | Kagawa et al. | 524/451 |
| 5,236,625 | 8/1993 | Bardo et al. | 261/24 |
| 5,236,963 | 8/1993 | Jacoby et al. | 521/92 |
| 5,241,031 | 8/1993 | Mehta | 526/348.1 |

| | | | |
|---|---|---|---|
| 5,244,482 | 9/1993 | Hassenboehler, Jr. | 55/528 |
| 5,244,716 | 9/1993 | Thornton et al. | 428/198 |
| 5,250,612 | 10/1993 | Hazlitt et al. | 525/53 |
| 5,261,899 | 11/1993 | Visscher et al. | 604/367 |
| 5,263,949 | 11/1993 | Karami et al. | 604/383 |
| 5,277,970 | 1/1994 | Schuhmann et al. | 428/323 |
| 5,277,976 | 1/1994 | Hogle et al. | 428/397 |
| 5,284,540 | 2/1994 | Roth et al. | 156/160 |
| 5,288,791 | 2/1994 | Collier, IV et al. | 524/505 |
| 5,296,289 | 3/1994 | Collins | 428/296 |
| 5,300,365 | 4/1994 | Ogale | 428/461 |
| 5,317,035 | 5/1994 | Jacoby et al. | 521/143 |
| 5,318,842 | 6/1994 | Ogale | 428/349 |
| 5,324,576 | 6/1994 | Reed et al. | 428/288 |
| 5,326,612 | 7/1994 | Goulait | 428/100 |
| 5,326,625 | 7/1994 | Schuhmann et al. | 428/215 |
| 5,331,047 | 7/1994 | Giacobbe | 525/88 |
| 5,332,613 | 7/1994 | Taylor et al. | 428/152 |
| 5,354,591 | 10/1994 | Ott et al. | 428/99 |
| 5,372,882 | 12/1994 | Peiffer et al. | 428/34.9 |
| 5,376,430 | 12/1994 | Swenson et al. | 428/152 |
| 5,382,400 | 1/1995 | Pike et al. | 264/168 |
| 5,382,461 | 1/1995 | Wu | 428/86 |
| 5,382,462 | 1/1995 | Pacione | 428/95 |
| 5,385,972 | 1/1995 | Yamamoto et al. | 524/579 |
| 5,397,635 | 3/1995 | Wood, Jr. | 428/314.4 |
| 5,407,439 | 4/1995 | Goulait | 604/391 |
| 5,409,761 | 4/1995 | Langley | 428/198 |
| 5,422,172 | 6/1995 | Wu | 428/230 |
| 5,445,862 | 8/1995 | Kaneko et al. | 428/148 |
| 5,453,318 | 9/1995 | Giacobbe | 428/286 |
| 5,470,639 | 11/1995 | Gessner et al. | 428/152 |
| 5,476,702 | 12/1995 | Datta et al. | 428/99 |
| 5,498,461 | 3/1996 | Rockney | 428/100 |
| 5,539,056 | 7/1996 | Yang et al. | 525/240 |
| 5,569,233 | 10/1996 | Goulait | 604/391 |
| 5,582,923 | 12/1996 | Kale et al. | 428/523 |
| 5,595,567 | 1/1997 | King et al. | 604/391 |
| 5,596,052 | 1/1997 | Resconi et al. | 526/127 |
| 5,599,420 | 2/1997 | Yeo et al. | 156/290 |
| 5,605,735 | 2/1997 | Zehner et al. | 428/100 |
| 5,614,281 | 3/1997 | Jackson et al. | 428/100 |
| 5,616,394 | 4/1997 | Gorman et al. | 428/99 |
| 5,616,420 | 4/1997 | Yamaoka et al. | 428/515 |
| 5,620,779 | 4/1997 | Levy et al. | 428/167 |
| 5,624,991 | 4/1997 | Harada et al. | 524/451 |
| 5,626,571 | 5/1997 | Young et al. | 604/370 |
| 5,628,097 | 5/1997 | Benson et al. | 28/165 |
| 5,647,864 | 7/1997 | Allen et al. | 604/391 |
| 5,695,868 | 12/1997 | McCormack | 428/283 |

FOREIGN PATENT DOCUMENTS

| | | |
|---|---|---|
| 97/04955 | 2/1997 | (WO) . |
| 97/11661 | 4/1997 | (WO) . |
| 97/11662 | 4/1997 | (WO) . |
| 97/24482 | 7/1997 | (WO) . |
| 98/04397 | 2/1998 | (WO) . |
| 99/14045 | 3/1999 | (WO) . |
| 99/14046 | 3/1999 | (WO) . |

OTHER PUBLICATIONS

"Don't Say 'Metallocene,' Say 'Single–Site'", by Jan. H. Schut, Plastics World, Apr. 1997, pp. 27–32.

"Here's the Latest Score on Single Site Catalysts", by Jan H. Schut, Plastics World, Apr., 1997, pp. 41–46.

U.S. application No. 08/754,419, filed Dec. 17, 1996, "Pattern–Unbonded Nonwoven Web and Process for Making the Same".

U.S. application No. 08/929,432, filed Sep. 15, 1997, "Breathable Barrier Composite Useful as an Ideal Loop Fastener Component".

U.S. application No. 08/929,561, filed Sep. 15, 1997 "Stretch–Pillowed Bulked Laminate Useful as an Ideal Loop Fastener Component".

LAMINATE HAVING IMPROVED BARRIER PROPERTIES

This application is a continuation-in-part of U.S. patent application Ser. No. 08/929,432 filed Sep. 15, 1997 now U.S. Pat. No. 5,997,981 entitled "Breathable Barrier Composite Useful as an Ideal Loop Fastener Component", now U.S. Pat. No. 5,997,981, which is incorporated herein in its entirety by reference.

BACKGROUND OF THE INVENTION

1. Field of the Invention

The invention is directed to laminates that have clothlike attributes and that act as barriers to passage of liquids and have improved resistance to viral passage. There are numerous uses for such laminates including disposable and limited use apparel such as surgeon's gowns and industrial workwear. Other applications include components of personal care products like disposable diapers, training pants, incontinence wear and feminine hygiene products. Barrier needs vary for such products, but are critical for medical products such as surgical drapes and gowns, for example. Film components can provide absolute barrier properties but are often uncomfortable and lack the ability to pass moisture vapor, i.e. breathe, while conventional nonwovens do not provide adequate protection for many applications. Laminates of breathable, lightweight films with nonwovens can meet the needs of many applications but, when bonded conventionally, compromise barrier protection for the most demanding medical applications. The field includes laminates having improved barrier properties especially adapted for such medical and other uses where improved barrier is especially important.

2. Background

The art is replete with references to laminates of films and nonwovens for medical and other applications. For example, coassigned U.S. Pat. No. 4,379,192 to Wahlquist and Shultz describes such laminates formed by a patterned application of heat and pressure to combined layers of a meltblown nonwoven and a polymeric film. The laminate is both an absorbent and an impervious barrier for medical applications. It is also known, for example, as taught in coassigned U.S. Pat. No. 5,695,868 to McCormack, to form laminates including breathable films for use as backing components of, e.g. disposable diapers. Particularly for medical applications demanding a high barrier level to viral penetration, it remains desired to provide a breathable material having improved barrier properties at a cost consistent with disposability and single use applications.

SUMMARY OF THE INVENTION

The present invention is directed to a laminate of a pattern prebonded nonwoven and a film as well as to the process for making such a laminate and applications for the laminate as a high barrier material that can have breathable, clothlike attributes. In accordance with the invention, the film preferentially bonds to the nonwoven in the pattern prebond areas and bonding can be achieved without deleteriously affecting the integrity of the film in the bond areas. In a preferred aspect for medical applications, the film is thin and microporous while maintaining the desired barrier levels to viral penetration. Bonding may be achieved thermally by smooth calendering without requiring added adhesive wherein the smooth roll bonding will generally maintain substantially uniform film thickness in the laminate. Advantageous embodiments include polyolefin spunbonded nonwovens bonded to a coextruded film of mLLDPE (metallocene or "single site" catalyzed polyethylene) or conventional LLDPE (linear low density polyethylene) using a bonding layer containing an amorphous polymer (for example, less than 30% crystallinity) of a "single site" (or metallocene) catalyzed LLDPE and/or other amorphous polymer(s) in face-to-face contact with the spunbond nonwoven. The amorphous bonding layer may, and for most applications will, include up to 75%, frequently between about 45% to about 70% of a filler as described in more detail below. The polymer component of the bonding layer may also include a crystalline component, frequently in the amount of from about 45% to 75%, and may also include other polymers for reduced cost or to impart desired properties or improve processing so long as such additional components do not result in a laminate peel strength, as described below, of less than about 25 grams, desirably not less than about 45 grams. The nonwoven layer contains a bond pattern of either uniform or nonuniform bond impressions that result in an unbonded area of at least about 80% taken over any 100 cm square of nonwoven surface. In addition, the bond frequency provides a pattern density in the range of from about 100 to about 600 bonds/in.$^2$, advantageously about 200 to about 500 bonds/in$^2$. The film layer is either a multilayer or coextruded structure with an exposed layer of a soft, amorphous polymer as previously described, or a monolayer that is amorphous as described, having adhesive properties and, in either case, can be a microporous liquid barrier that is conformable and compatible with the nonwoven component. To enhance clothlike aesthetics, a retracted laminate can be formed by stretching the film prior to lamination to the nonwoven and subsequently allowing the laminate to relax or retract producing a textured surface of unbonded inter-bond filaments or fibers between bond areas where the film and nonwoven remain securely attached. The invention also includes the method for making the laminate which desirably is carried out as an inline process to avoid the need to store rolls of the amorphous-layer film.

DETAILED DESCRIPTION

Definitions

As used herein the following terms have the specified meanings unless the context demands a different meaning or a different meaning is expressed; also, the singular generally includes the plural, and the plural generally includes the singular unless otherwise indicated.

"Nonwoven" means a web of fibers or filaments that is formed by means other than knitting or weaving and that contains bonds between some or all of the fibers or filaments; such bonds may be formed, for example, by thermal, adhesive or mechanical means such as entanglement.

"Fiber" means an elongated strand of defined length, such as staple fibers formed by cutting a continuous strand into lengths of, for example, 2 to 5 cm. Collections of fibers may have the same or different lengths.

"Filament" means a generally continuous strand that has a very large ratio of length to diameter, for example, 1000 or more.

"Spunbond" means a nonwoven of filaments formed by melt extrusion of a polymer into strands that are quenched and drawn, usually by high velocity air, to strengthen the filaments which are collected on a forming surface and bonded, often by the patterned application of heat and pressure. Spunbonded processes are described, for example, in the following patents to which reference may be made for additional details: U.S. Pat. No. 4,340,563 to Appel et al., U.S. Pat. No. 3,802,817 to Matsuki et al., and U.S. Pat. No. 3,692,618 to Dorschner et al.

"Amorphous Polymer", when used herein to describe a bonding layer either as a multilayer film component or separately applied layer, means a thermoplastic polymer such as certain polyolefins with density in the range of from about 0.85 to about 0.94 g/cc, desirably about 0.85 to about 0.89, and low crystallinity, for example less than about 30%, such as those frequently used as components of adhesives and having limited hot melt properties.

"Thermal point-bonding" involves passing a fabric or web of fibers to be bonded between a heated calender roll and an anvil roll. The calender roll is patterned in some way so that the entire fabric is not bonded across its entire surface. Many patterns for calender rolls have been developed for functional as well as aesthetic reasons. As will be understood by those skilled in the art, bond area percentages are, of necessity, described in approximations or ranges since bond pins are normally tapered and wear down over time. As those skilled in the art will also recognize, references to "pins/in.$^2$" and "bonds/in.$^2$" are somewhat interchangeable since the anvil pins will create bonds in the substrate in essentially the same sizes and surface relationship as the pins on the anvil. One example of a pattern has points and is the Hansen Pennings or "H&P" pattern with about 200 bonds/square inch as taught in U.S. Pat. No. 3,855,046 to Hansen and Pennings. The H&P pattern has square point or pin bonding areas wherein each pin may have a side dimension of 0.038 inches (0.965 mm), for example, resulting in a pattern having a bonded area of about 30%. Another typical point bonding pattern is the expanded Hansen and Pennings or "EHP" bond pattern which produces a bond area of about 15% to 18% which may have a square pin having a side dimension of 0.037 inches (0.94 mm), for example, and a pin density of about 100 pins/in$^2$. Another typical point bonding pattern designated "714" has square pin bonding areas wherein each pin may have a side dimension of 0.023 inches, for example, for a bond area of 15% to 20% and about 270 pins/in$^2$. Other common patterns include a "Ramisch" diamond pattern with repeating diamonds having a bond area of 8% to 14% and 52 pins/in$^2$, as well as a wire weave pattern looking as the name suggests, e.g. like a window screen and having a bond area of 15% to 20% and 302 bonds/in.$^2$. Typically, the percent bonding area varies widely from around 10% to around 30% of the area of the fabric laminate web and the number of pins/in$^2$ also may vary over a wide range. Of the practically limitless combinations of bond configurations, however, only selected bond patterns are useful in accordance with the invention. These will have a bond area in the range of from about 5% to about 40%, desirably in the range of from about 10% to about 25%, and a bond frequency in the range of from about 100 to about 600 per square inch, desirably in the range of from about 200 to about 500 per square inch. When used herein, the term "prebonded" nonwoven means those nonwovens having been bonded with a pattern defined as useful in accordance with these parameters. As is well known in the art, the spot bonding of such thermal pattern calendered webs holds the laminate layers together as well as imparts a measure of integrity to each individual layer by bonding filaments and/or fibers within each layer. As is also known, flexibility of the web may be affected by selection of a bond pattern since filaments may remain unbonded between bond points and free to move to allow the web to flex. In contrast, webs that are overall bonded or bonded at each fiber contact point, such as extrusion coated or solvent bonded webs, tend to resist flexing and are stiffer.

Test Procedures

Hydrohead: A measure of the liquid barrier properties of a fabric is the hydrohead test. The hydrohead test determines the height of water (in mbars) which the fabric will support before a predetermined amount of liquid passes through. A higher hydrohead reading indicates that a fabric is a better barrier to liquid penetration than a fabric with a lower hydrohead. The hydrohead test is performed according to Federal Test Standard 191A, Method 5514.

Water Vapor Transmission Rate Test: The water vapor transmission rate (WVTR) for the sample materials was calculated in general accordance with ASTM Standard E96-80. Circular samples measuring three inches in diameter were cut from each of the test materials and a control, which was a piece of CELGARD® 2500 film from Hoechst Celanese Corporation of Sommerville, N.J. CELGARD® 2500 film is a microporous polypropylene film. Three specimens were prepared for each material. The test dishes were number 681 Vapometer cups distributed by Thwing-Albert Instrument Company of Philadelphia, Pa. One hundred milliliters (ml) of distilled water was poured into each Vapometer cup and individual samples of the test materials and control material were placed across the open tops of the individual cups. Screw-on flanges were tightened to form a seal along the edges of each cup (no sealant grease was used), leaving the associated test material or control material exposed to the ambient atmosphere over a 6.5 centimeter (cm) diameter circle having an exposed area of approximately 33.17 square centimeters. The cups were weighed and placed in a forced air oven set at a temperature of 37° C. (100° F.). The oven was a constant temperature oven with external air circulating through it to prevent water vapor accumulation inside. A suitable forced air oven is, for example, a Blue M Power-O-Matic 60 oven distributed by Blue M Electric Co. of Blue Island, Ill. After 24 hours, the cups were removed from the oven and weighed again. The preliminary test water vapor transmission rate values were calculated as follows:

Test $WVTR$=(grams weight loss over 24 hours)×315.5 (g/m$^2$/24 hrs)

The relative humidity within the oven was not specifically controlled.

Under predetermined set conditions of 100° F. (37° C.) and ambient relative humidity, the WVTR for the CELGARD® 2500 film control has been determined to be 5000 grams per square meter for 24 hours (g/m$^2$/24 hrs). Accordingly, the control sample was run with each test and the preliminary test values were corrected to set condition using the following equation:

$WVTR$=(Test $WVTR$/control $WVTR$)×5000 g/m$^2$/24 hrs (g/m$^2$/24 hrs)

Strip Tensile: The strip tensile measures the peak and breaking loads and peak and break percent elongations of a fabric or film. This test measures the load (strength) in grams and elongation in percent. In the strip tensile test, two clamps, each having two jaws with each jaw having a facing in contact with the sample, hold the material in the same plane, usually vertically, separated by 3 inches and move apart at a specified rate of extension. Values for strip tensile strength and strip elongation are obtained using a sample size of 3 inches by 6 inches, with a jaw facing size of 1 inch high by 3 inches wide, and a constant rate of extension of 300 mm/min. The Sintech 2 tester, available from the Sintech Corporation, 1001 Sheldon Dr., Cary, N.C. 27513, the Instron Model TM, available from the Instron Corporation, 2500 Washington St., Canton, Mass. 02021, or a Thwing-Albert Model INTELLECT II available from the Thwing-Albert Instrument Co., 10960 Dutton Rd., Philadelphia, Pa. 19154 may be used for this test. Reported results are the average of three specimens tested and the test may be performed with the specimen in the cross direction (CD) or in the machine direction (MD).

Peel Test: In peel or delamination testing a laminate is tested for the amount of tensile force which will pull the layers of the laminate apart. Values for peel strength are obtained using a specified width of fabric, clamp jaw width and a constant rate of extension. For samples having a film side, the film side of the specimen is covered with masking tape, or some other suitable material, in order to prevent the film from ripping apart during the test. The masking tape is on only one side of the laminate and so does not contribute to the peel strength of the sample. This test uses two clamps, each having two jaws with each jaw having a facing in contact with the sample, to hold the material in the same plane, usually vertically, separated by 2 inches to start. The sample size is 4 inches wide by as much length as necessary to delaminate enough sample length. The jaw facing size is 1 inch high by at least 4 inches wide, and the constant rate of extension is 300 mm/min. The sample is delaminated by hand a sufficient amount to allow it to be clamped into position, and the clamps move apart at the specified rate of extension to pull the laminate apart. The sample specimen is pulled apart at 1800 of separation between the two layers, and the peel strength reported is an average of three tests, peak load in grams. Measurement of the force begins when 16 mm of the laminate has been pulled apart, and it continues until a total of 170 mm has been delaminated. The Sintech 2 tester, available from the Sintech Corporation, 1001 Sheldon Dr., Cary, N.C. 27513, the Instron Model TM, available from the Instron Corporation, 2500 Washington St., Canton, Mass. 02021, or the Thwing-Albert Model INTELLECT II available from the Thwing-Albert Instrument Co., 10960 Dutton Rd., Philadelphia, Pa. 19154, may be used for this test. The test may be performed with the specimen in the cross direction (CD) or in the machine direction (MD).

Martindale Abrasion Test: This test measures the relative resistance to abrasion of a fabric. The test results are reported on a scale of 1 to 5, with 5 being the least wear and 1 the most, after 120 cycles with a weight of 1.3 pounds per square inch. The test is carried out with a Martindale Wear and Abrasion Tester such as Model no. 103 or Model no. 403 available from James H. Heal & Company, Ltd. of West Yorkshire, England. The abradant used is a 36 inch by 4 inch by 0.05 thick silicone rubber wheel reinforced with fiberglass having a rubber surface hardness 81A Durometer, Shore A of 81 plus or minus 9. The abradant is available from Flight Insulation Inc., a distributor for Connecticut Hard Rubber, 925 Industrial Park, NE, Marietta, Ga. 30065.

Basis Weight: the basis weights of various materials described herein were determined in accordance with Federal Test Method No. 191A/5041. Sample size for the sample materials was 15.24×15.24 centimeters, and three values were obtained for each material and then averaged. The values reported below are the averages in units of grams per square meter (gsm).

Viral Barrier results were measured in accordance with ASTM F1671-97a. In this test a specimen is subjected to a nutrient broth containing a virus for a specified time and pressure sequence. Visual detection of penetration is supplemented with an assay procedure that will detect viable viruses which penetrate the material even when liquid penetration is not visible. Any evidence of viral penetration for a test specimen constitutes failure. For the tests reported, Procedure A (unsupported specimen) was used.

Blood Barrier results were obtained in accordance with ASTM F1670-95. This test procedure is similar to ASTM F1671-97a except that synthetic blood simulant is used as the challenge material, and visual observation, alone, is used to determine when, or if, penetration occurs. Results are reported as pass ("compliant") or fail.

As used herein the term "uniform film thickness" or "constant film thickness" means that the cross sectional thickness of the film in the laminate as measured by SEM (scanning electron microscopy) at a magnification of at least 1000X and based on an average of 10 readings within bond areas and outside bond areas does not vary by more than about 25% and, for many applications, does not vary by more than 10%.

DETAILED DESCRIPTION OF EMBODIMENTS

The invention will be described with reference to the drawings and examples which illustrate certain embodiments. It will be apparent to those skilled in the art that these embodiments do not represent the full scope of the invention which is broadly applicable in the form of variations and equivalents as may be embraced by the claims appended hereto. It is intended that the scope of the claims extend to all such variations and equivalents.

As will be apparent to those skilled in the art, the process and barrier material of the invention are adaptable to many films and pattern prebonded nonwoven layers to produce barrier and breathable barrier materials having widely varying properties. To work effectively as a barrier material in accordance with the invention, however, selection of these components desirably takes into consideration a number of factors. The film, for example, must be robust enough to withstand the process at the low basis weights necessary to provide desired flexibility and softness as well as to maintain low cost. In addition the film must be capable of bonding effectively to the nonwoven layer and maintaining barrier properties and, when desired, moisture vapor transmission rates. For some applications it is advantageous that the composite is also made opaque.

Films meeting these requirements include polymers, such as polyethylene, polypropylene, blends including polyolefins and copolymers such as ethylene and propylene copolymers, for example, generally having a basis weight in the range of from about 10 gsm to about 50 gsm, advantageously for barrier component applications, in the range of from about 15 gsm to about 30 gsm. The film thickness prior to stretching will frequently be in the range of from about $10\mu$ to $30\mu$ and advantageously for many applications between about $15\mu$ to about $20\mu$. Specific examples include linear low density polyethylenes such as Dowlex® 2035, NG3347, NG3310, AFFINITY® PT1409 and Elite® 5200 available from Dow Chemical Company of Midland, Mich. The film compositions desirably contain at least about 40% by weight of a filler such as calcium carbonate and especially about 45% to about 70% by weight of such film. Filler examples include Supercoat® calcium carbonate from English China Clay of Sylacauga, Ala., which contains a coating of about 1.5% by weight of either stearic acid or behenic acid to enhance dispersion of the filler. Particularly advantageous film examples include coextruded films having on one or both sides an external layer of an amorphous polymer, such as a propene-rich polyalphaolefin terpolymer or copolymer, which allows bonding to the facing layer without requiring a separately applied bonding layer. In addition, the amorphous polymer layer may also include hot melt adhesives or other amorphous polyalphaolefin resins, which desirably have a melt viscosity of 100,000 mPa.sec or greater, in an amount of, for example, up to about 50% by weight of the polymer fraction, so long as the above described breathable barrier properties are retained. Generally, other examples of bonding agents include, but are not limited to, polyamides, ethylene copolymers such as ethylene vinyl acetate (EVA), ethylene ethyl acrylate (EEA), ethylene acrylic acid (EAA), ethylene methyl acrylate (EMA) and ethylene normal-butyl acrylate (ENBA), wood rosin and its derivatives, hydrocarbon resins, polyterpene resins, atactic polypropylene and amorphous polypropylene. Also included are predominantly amorphous ethylene propylene copolymers commonly known as ethylene-propylene rubber (EPR) and a class of materials referred to as toughened polypropylene (TPP) and olefinic thermoplastic polymers where EPR is mechanically dispersed or molecularly dispersed via in-reactor multistage polymerization in polypropylene or polypropylene/polyethylene blends. Commercially available amorphous polyalphaolefins, such as those used in hot melt adhesives, are suitable for use with the present invention and include, but are not limited to, REX-TAC® ethylene-propylene APAO E-4 and E-5 and butylene-propylene BM-4 and BH-5, and REXTAC® RT2301, RT2503A, RT2780 and RT2557-52R from Huntsman Corporation of Odessa, Tex., and VESTOPLAST® 792 from Huls AG of Marl, Germany. These amorphous polyolefins are commonly synthesized on a Ziegler-Natta supported catalyst and an alkyl aluminum co-catalyst, and the olefin, such as propylene, is polymerized in combination with varied amounts of one or more of ethylene, 1-butene, 1-hexene, or other materials to produce a predominantly atactic hydrocarbon chain. An example of a different class of amorphous polymers is Catalloy® polymer from Montell USA, Inc. of Wilmington, Del., which is an olefinic multistep reactor product wherein an amorphous ethylene propylene random copolymer is molecularly dispersed in a predominantly semicrystalline high-per-cent propylene monomer/low-per-cent ethylene monomer continuous matrix, an example of which is described in U.S. Pat. No. 5,300,365 to Ogale. Also useful are certain elastomeric polypropylenes such as are described, for example, in U.S. Pat. No. 5,539,056 to Yang et al. and U.S. Pat. No. 5,596,052 to Resconi et al., incorporated herein by reference in their entireties, and polyethylenes such as AFFINITY® EG 8200 from Dow Chemical of Midland, Mich. as well as EXACT® 4049, 4011 and 4041 from Exxon of Houston, Tex., as well as blends. A composite with the bonding layer on one side only may have the advantage of a higher moisture vapor transmission rate if desired. Such films are described in greater detail in coassigned U.S. patent application Ser. No. 929,562 filed on Sep. 15, 1997 in the names of McCormack and Haffner and entitled "Breathable Filled Film Laminate", now U.S. Pat. No. 6,045,900, the contents of which are incorporated herein in their entirety by reference. Other film layers will be apparent to those skilled in the art in light of the examples provided herein.

The pattern prebonded nonwoven layer will be selected so as to be compatible with the film or bonding layer and will have properties such as basis weight, bulk, and strength adequate for the intended use. Primarily for economic reasons, nonwoven webs are preferred, especially spunbonded nonwovens having a basis weight generally in the range of from about 10 gsm to about 50 gsm, for example, frequently within the range of from about 15 gsm to about 25 gsm. The composition of the nonwoven layer will be selected to be compatible with the film layer while providing the desired properties in the intended application. Generally useful are synthetic polymers such as polyolefins, for example, polypropylene, polyethylene, blends, and copolymers including propylene and ethylene. Such nonwovens are described above and in the references provided herein, and their manufacture is known to those skilled in this art. Specific examples include ACCORD® spunbond nonwovens available from Kimberly-Clark Corporation, Dallas, Tex. The bond pattern for the facing layer, as mentioned above, will provide for looping between bonds as may be desired to provide clothlike attributes. Useful examples include HHD pattern, which comprises point bonds having about 460 pins/in.$^2$ for a bond area of about 15% to about 23%, a wireweave pattern which, as the name suggests, has the appearance of a windowscreen and about 302 pins/in$^2$ with a bond area of about 15% to about 20% and a Ramish pattern as above described. One advantageous bond pattern for a spunbond facing web is a "S" weave pattern as described in coassigned U.S. patent application Ser. No. 929,808 filed on Sep. 15, 1997 in the names of McCormack, Fuqua, and Smith, and entitled "Nonwoven Bonding Patterns Producing Fabrics with Improved Strength and Abrasion Resistance", now U.S. Pat. No. 5,964,742, which is incorporated herein by reference in its entirety. In all cases the % bond area will be in the range generally between about 5% and about 40% and frequently between about 10% and about 25% and bond density from about 100 to about 600/in.$^2$, often in the range of from about 200/in.$^2$ to about 500 in$^2$. In addition, for garment and surgical drape component applications, the nonwoven will desirably have a tensile strength, measured as described above, of at least about 3000 g taken in the machine direction, and at least about 1500 g taken in the cross-machine direction, and advantageously a Martindale abrasion, measured as described above, of at least about 3.

The amorphous polymer bonding layer will adhere to both facing and film layers and, if desired, provide bonding as a monolayer or coextruded film component between them without interfering with moisture vapor transmission. Advantageously the bonding layer is provided as a coextruded component of the film layer itself.

The bond strength between the nonwoven and the film, as measured by the above described laminate peel test, will desirably be at least about 25 g, advantageously at least about 45 g or, in some cases at least about 60 g so as to prevent undesired delamination in use. In addition, for many applications and particularly as a surgical gown fabric, for example, the composite will have a hydrohead, as measured by the above described hydrohead test, of at least about 50 mbar of water and advantageously at least about 90 mbar. Moreover, the composite will desirably pass the test for resistance to viral penetration as described above. Especially when used as a surgical gown fabric, the composite will have a moisture vapor transmission rate of at least about 300 g/m²/24 hours and advantageously at least about 800 g/m²/24 hours, with rates of at least about 3000 g/m²/24 hours providing added comfort.

Figure 1:
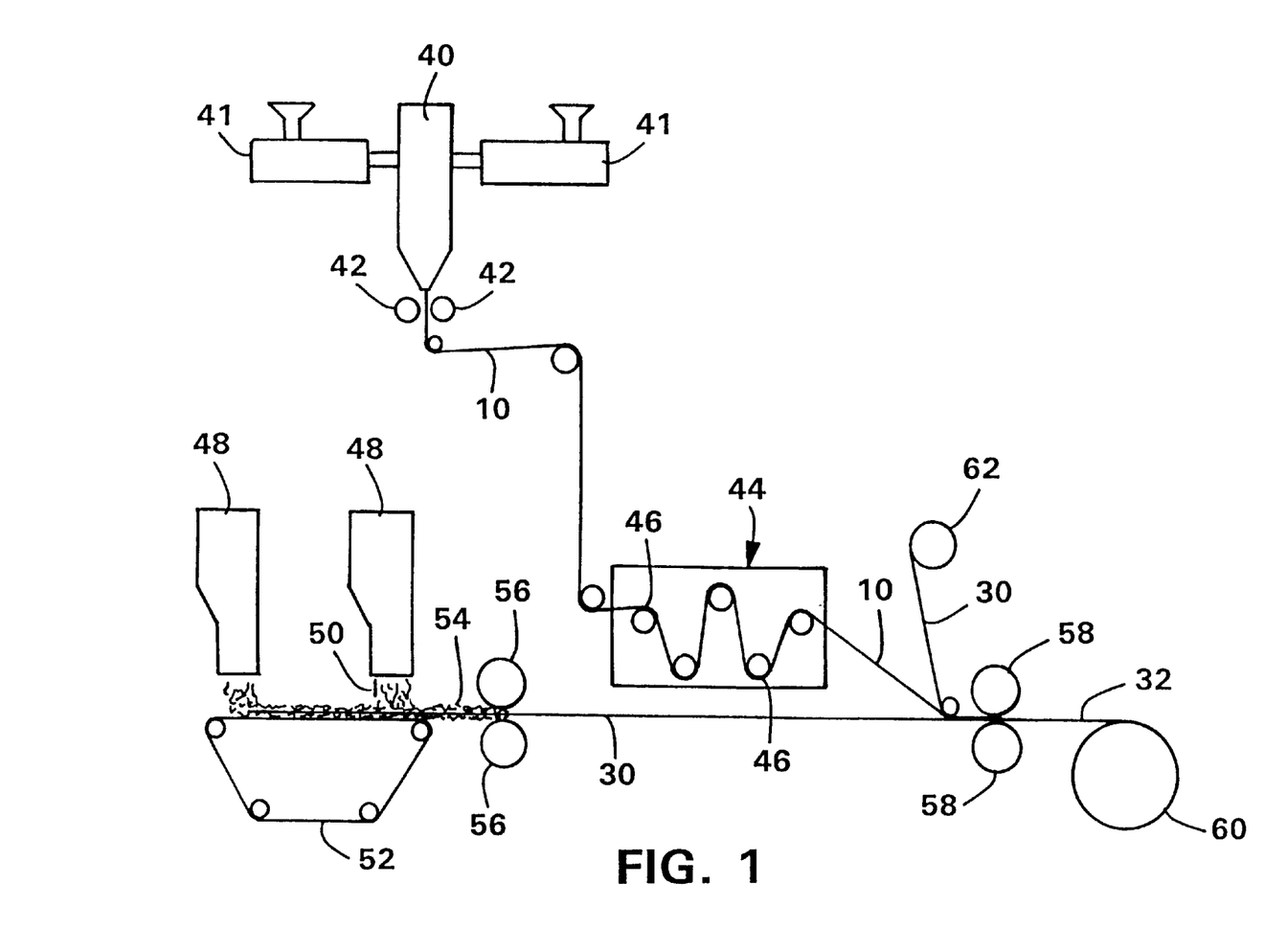
FIG. 1 is a schematic illustration of a process for making the improved barrier laminate of the present invention.

Referring to FIG. 1, a process for forming the multilayer film 10 is shown. A multilayer film 10 is formed from a coextrusion film apparatus 40 such as a cast or blown unit. Typically the apparatus 40 will include two or more polymer extruders 41 or a single extruder in the case where a monolayer film is formed. The film 10 is extruded into a pair of nip or chill rollers 42 one of which may be patterned so as to impart an embossed pattern to the newly formed film 10. This is particularly advantageous to reduce the gloss of the film and give it a matte finish. Typically, the film 10, as initially formed, will have an overall thickness 28 of approximately 25 to 60 μm with, in the case of multilayer films, the first or bonding layer having an initial thickness that may be about 5% to 50% of the total thickness, for example.

From the coextrusion film apparatus 40 the film 10 is directed to a film stretching unit 44 such as a machine direction orienter which is a commercially available device from vendors such as the Marshall and Williams Company of Providence, R.I. Such an apparatus 44 has a plurality of stretching rollers 46 which progressively stretch and thin the film 10 in the machine direction of the film which is the direction of travel of the film 10 through the process as shown in FIG. 1. After exiting the film stretching unit 44 the film 10 should have a reduced thickness depending on the degree of stretching applied.

The monolayer or multilayer film 10 may be immediately bonded to one or more support layers 30 to form a multilayer film/nonwoven laminate 32. Referring again to FIG. 1, a conventional fibrous nonwoven web forming apparatus 48, such as a pair of spunbond machines, is used to form the support layer 30. The long, essentially continuous filaments 50 are deposited onto a forming wire 52 as an unbonded web 54 and the unbonded web 54 is then sent through a pair of bonding rolls 56 to apply a prebond pattern and bond the filaments together and increase the tear strength of the resultant web support layer 30. One or both of the rolls are often heated to aid in bonding. One of the rolls 56 is also patterned so as to impart a discrete bond pattern with a prescribed bond surface area to the web 30. The other roll is usually a smooth anvil roll but this roll also may be patterned if desired. Once the multilayer or monolayer film 10 has been sufficiently thinned and oriented and the support layer 30 has been formed, the two components are brought together and laminated to one another using a pair of smooth laminating rolls 58. If desired, a third component such as another pattern bonded nonwoven 30 may be added by unwinding of roll 62, for example. As with the bonding rolls 56, the laminating rolls 58 may be heated. Once the laminate 32 exits the laminating rolls 58, it may be wound up into a roll 60 for subsequent processing. Alternatively, the laminate 32 may continue in-line for further processing or conversion.

The temperature to which the film 10 is heated will depend on the composition of the film as well as the breathability and other desired end properties of the composite material. In most cases the film will be heated to a temperature no higher than 10° C. below its melting point. The purpose for heating the film is to allow it to be stretched quickly without causing film defects. The amount of stretching will depend on the polymeric composition, but, in general, the film may be stretched to about 300% or more of its original length (that is, a one cm length, for example, will be stretched to 3 cm) but less than the amount that tends to result in film defects. For most applications with films based on polyolefins, for example, the stretch will be to at least 200% of the original film length and, frequently, in the range of about 250% to 500%. As will be explained in detail below, use of the amorphous polymer avoids the need for separate adhesive application and the laminate containing the amorphous polymer is softened by thermal energy at nip 58, for example. After nip 58, the two layers may be allowed to relax, with or without heating, and the laminate may be wound at a reduced speed, for example, 80% to 90% of the nip speed, permitting film 10 to retract to release filaments between the bond areas of facing layer 30 if desired. The combined layers may be annealed, if desired, by contact with heated roll (not shown) which is driven at about the speed of the retracted laminate to avoid significant additional stretching. The annealing temperature will vary according to the composition of the layers, but may be, for example, within 15° C. of the temperature used in stretching. After annealing, the combined layers may be cooled, for example, by contact with air from an air knife or chill rolls, if desired, or collected directly as roll 60, or directed to a converting line for incorporation into a personal care product. While not shown, an embossing step may be used, if desired, to impart an attractive pattern to the composite by, for example, passing it between embossing rolls in a manner well known to those skilled in this art.

Figure 2:
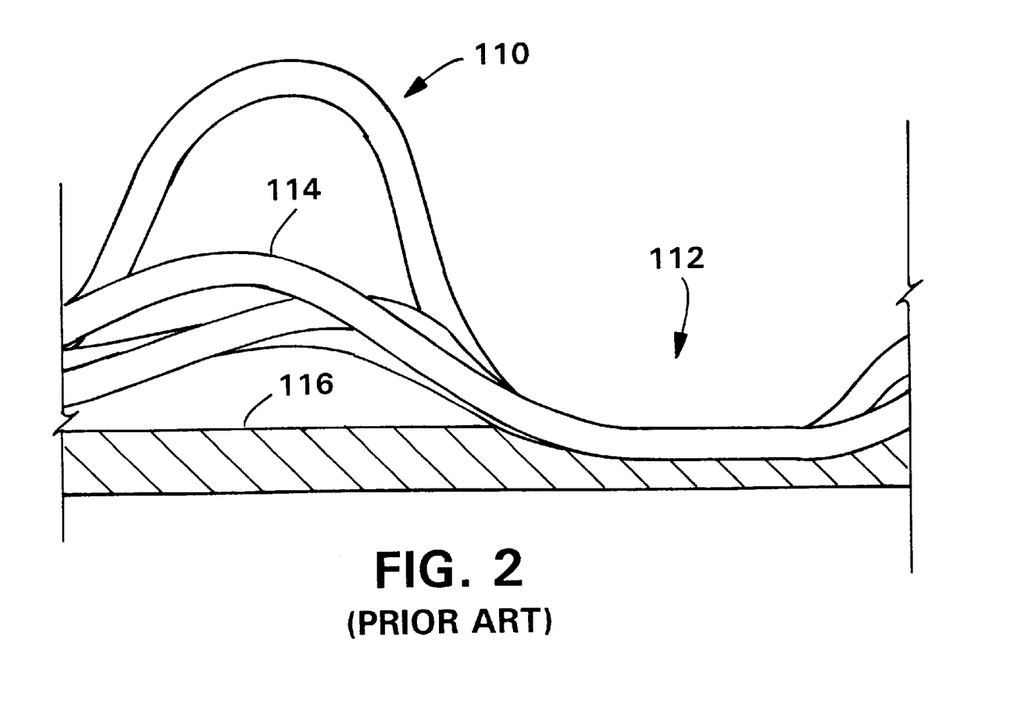
FIG. 2 is a schematic illustration in cross section of a laminate obtained by thermal spot bonding in accordance with prior art processes.

Referring to FIG. 2, there is shown in cross-section an embodiment of a composite formed by a patterned application of heat and pressure in a conventional manner. Unbonded areas 110 between bond areas 112 are formed in spunbonded facing layer 114 which is bonded to a film 116 at each of the thermal laminate bond points 112. As shown, the film thickness is reduced in the laminate bond point areas providing a potential for the integrity of the film to be compromised. This effect is typical of pattern heat and/or pressure bonding with either a monolayer film or a multilayer film with an amorphous bonding layer.

Figure 3:
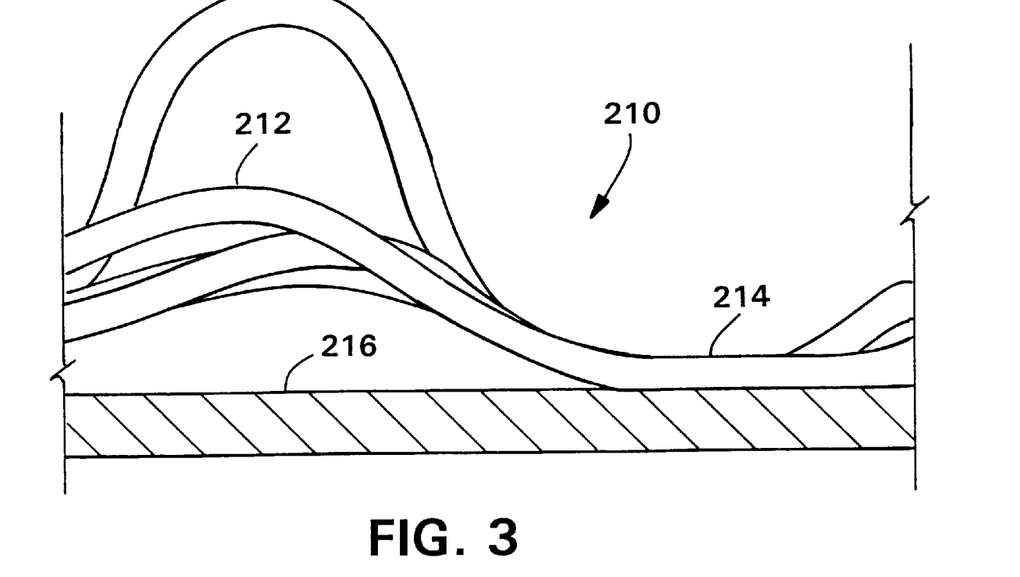
FIG. 3 is a view like FIG. 2 showing a laminate in accordance with the present invention.

Referring to FIG. 3, there is shown in a similar view to that of FIG. 2 a composite of the present invention. In this case composite 210 is a laminate of prebonded nonwoven layer 212 having a pattern of bond points 214, and monolayer film 216 bonded to nonwoven layer 212 at each of the prebond points 214. As shown, the thickness of film 216 is relatively constant and presents a reduced risk of barrier compromise.

Figure 3A:
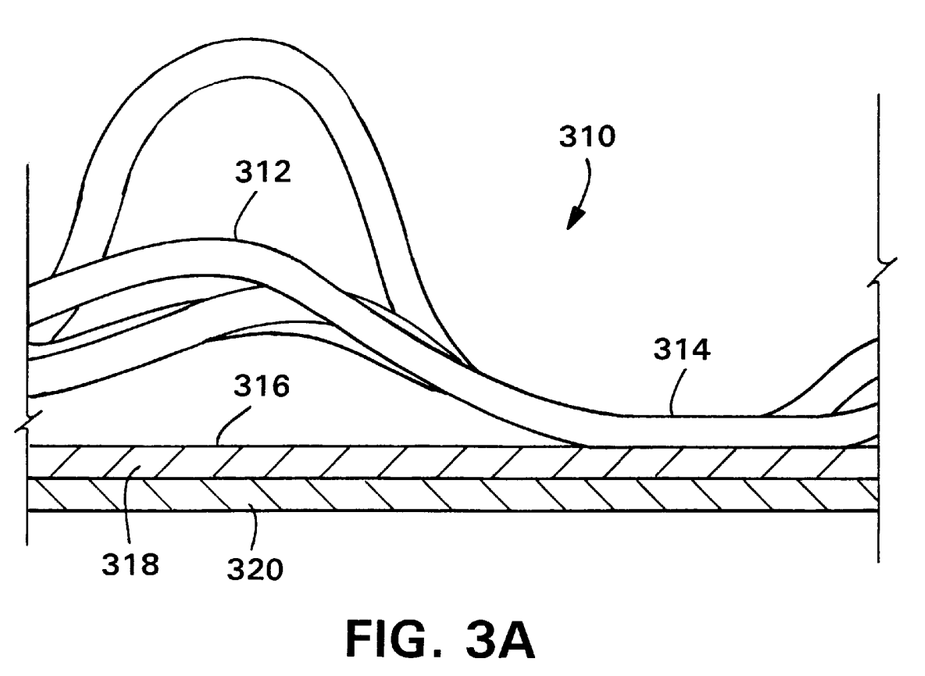
FIG. 3A is a view like FIG. 3 showing a laminate containing a two layer coextruded film laminate according to the present invention.

FIG. 3A is a view like that of FIG. 3 except the film includes multicomponents, base layer 320 and bonding layer 318. Again, the film is bonded to nonwoven 310 including filaments 312 at prebond point 314.

Figure 4:
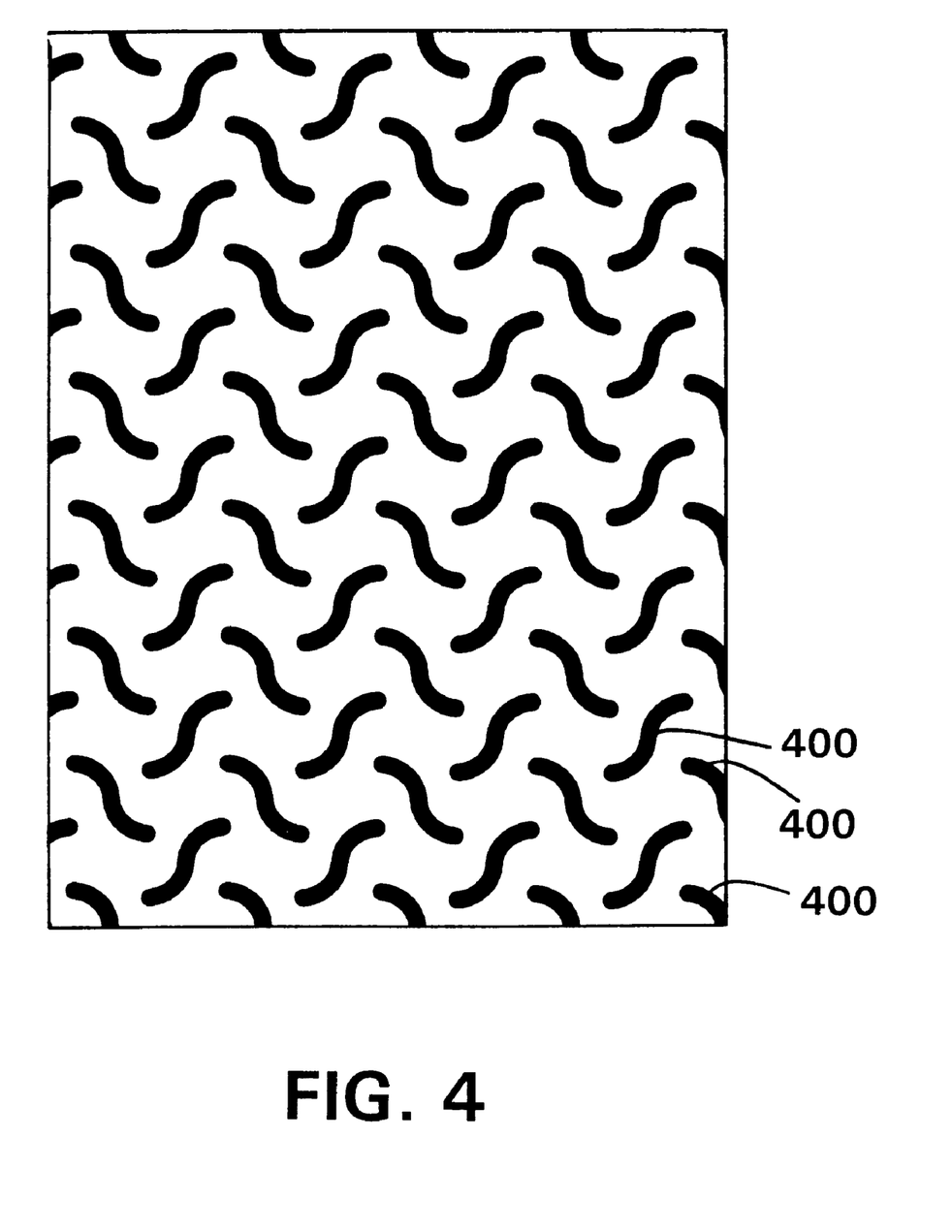
FIGS. 4 and 5 illustrate pattern prebonds useful with the present invention.
Figure 5:
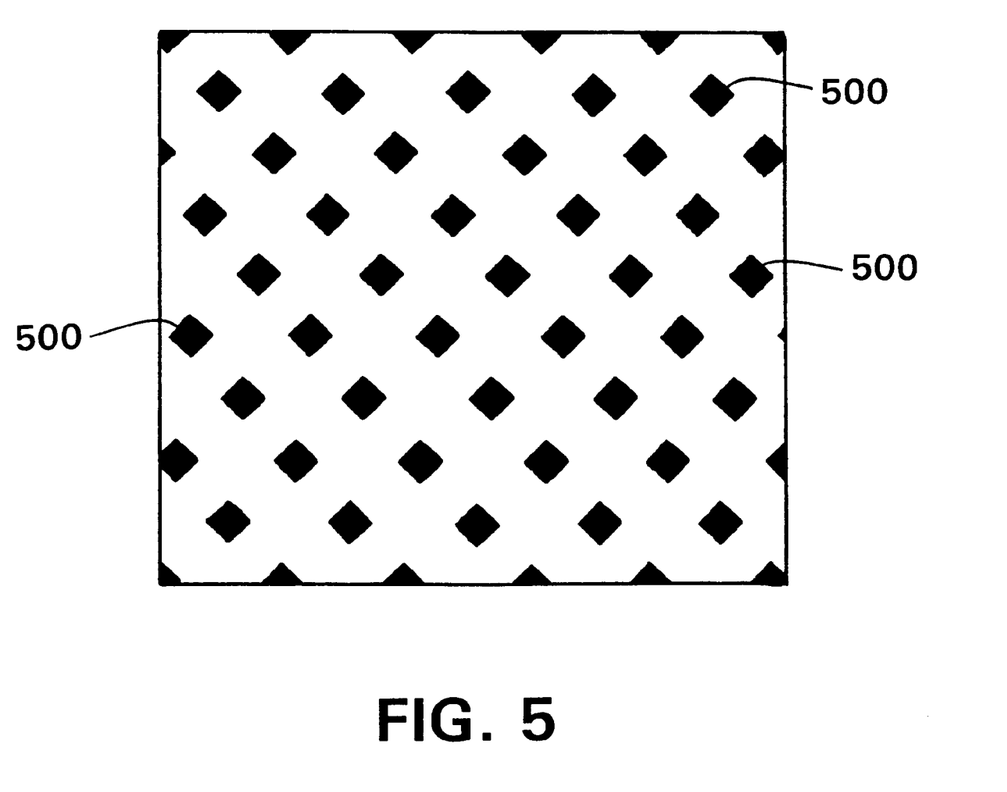

FIGS. 4 and 5 illustrate representative prebond patterns useful in accordance with the prebonded nonwoven component of the composite of the present invention. FIG. 4 shows "S-weave" as described above with prebond areas 400, and FIG. 5 shows "EHP" as described above with prebond areas 500.

EXAMPLE

For the following example a procedure as shown in FIG. 1 was used to form a composite, except as otherwise indicated.

Example 1

For this example, the film used was a cast coextruded "AB" film having a base layer which contained by weight 27% Dowlex 2035 (0.919 g/cc density, melt index at 190° C.

of 6 g/10 min), 23% Affinity PT 1409 (0.911 g/cc, melt index at 190° C. of 6 g/10 min), both available from Dow Chemical Co., 58% Supercoat™, a ground, stearic acid coated $CaCO_3$, available from English China Clay, and, for laminating to the spunbond, a bonding layer on one side which contained by weight 66% Supercoat™ $CaCO_3$, 8% Rextac® RT 2503A, an amorphous propene-rich polyalphaolefin from Huntsman Polymers, and 26% Affinity® EG 8200 (0.87 g/cc density, melt index at 190° C. of 5 g/10 min), an elastomeric polyethylene from Dow Chemical Co. The base layer constituted approximately 80% and the bonding layer 20% by weight of the total basis weight of the coextruded film which was 58 gsm (about 1.5 mils) prior to stretching. This film was preheated to 125° F. (52° C.), stretched at 140° F. (60° C.) in the machine direction to 3.8×ratio in a single zone, annealed at 199° F. (93° C.), and successfully in-line laminated to spunbond fabric at 197 ft/min (62 m/min) using a smooth steel roll (195° F. or 90° C.) nipped with 15 pounds per linear inch (PLI) force against a smooth rubber roll (Shore 40A hardness) which was not directly heated. The spunbond, about 20 gsm basis weight, was made of filaments of about 1.8 denier extruded from a copolymer of ethylene with 3.5% propylene (resin 6D43, available from Union Carbide Corp.), and it was prebonded with an "HDD" pattern (described previously). The laminate was allowed to retract 13% (from nip speed of 197 ft/min to the winder speed of 171 ft/min). The resulting laminate had a basis weight of 44 gsm, strip tensile MD break load of 10530 g at 55% strain, CD break load of 3835 g at 85% strain, laminate MD peel strength of 184 grams, unsupported hydrohead of 160 mbar, and WVTR of 4011 g/m$^2$/24 hours. When tested for blood penetration, the result was "compliant"(zero penetration) with ASTM F1670. Likewise, when tested for viral penetration, the result was "compliant" (zero penetration) with ASTM 1671. Three specimens were used for each of the tests.

Comparative Example

For this example, the film used was a cast coextruded "AB" film having a base layer which contained by weight 20% Dowlex 2035 (0.919 g/cc density, melt index at 190° C. of 6 g/10 min), 20% Affinity PT 1409 (0.911 g/cc, melt index at 190° C. of 6 g/10 min), both available from Dow Chemical Co., 60% Supercoat™, a ground, stearic acid coated $CaCO_3$, available from English China Clay, and, for laminating to the spunbond, a bonding layer on one side which contained by weight 70% Supercoat™ $CaCO_3$, 5% Vestoplast 792, an amorphous propene-rich polyalphaolefin from Huls America, Inc of Somerset, N.J., and 25% Affinity® EG 8200 (0.87 g/cc density, melt index at 190° C. of 5 g/10 min), an elastomeric polyethylene from Dow Chemical Co. The base layer constituted approximately 80% and the bonding layer 20% by weight of the total basis weight of the coextruded film which was 58 gsm (about 1.5 mils) prior to stretching. This film was preheated to 120° F. (49° C.), stretched at 130° F. (54° C.) in the machine direction to 4.0×ratio in a single zone, annealed at 215° F. (101° C.). This stretched film was subsequently in-line laminated to spunbond fabric at 431 ft/min (170 m/min) using an engraved patterned roll, for example, as shown in FIG. 4 of U.S. Pat. No. 5,599,420 to Yeo et al., the entire contents of which are incorporated herein by reference, at 241° F. (116° C.) against a smooth steel roll at 220° F. (104° C.), using a pressure of 72 pounds per linear inch (PLI) force. The spunbond, about 20 gsm basis weight, was made of filaments of about 1.8 denier extruded from a copolymer of ethylene with 3.5% propylene (resin 6D43, available from Union Carbide Corp.), and it was prebonded with an "HDD" pattern (described previously). The laminate was allowed to retract 5% (from nip speed of 431 ft/min to the winder speed of 408 ft/min). The resulting laminate had a basis weight of 1.35 osy (45 gsm), strip tensile MD break load of 9990 g at 53% strain, CD break load of 4460 g at 72% strain, unsupported hydrohead of 130 mbar, MVTR of 3750 g/m$^2$/24 hr, a laminate MD peel of 108 g. The sample failed synthetic blood penetration testing per ASTM F1670. Phage testing (ASTM 1671) was not performed because failure in the less stringent blood test indicated that the phage test would also fail.

Those of skill in this art will recognize that the invention is subject to many variations, modifications and equivalents within the scope of the foregoing description. It is intended that all such modifications, variations and equivalents be included as are embraced by the appended claims. For these purposes equivalents include functional as well as structural and compositional equivalents. For example, a nail and a screw are functional fastener equivalents even though they may be of different structures.

We claim:

1. A laminate compliant with ASTM F1670-95 having laminate bonds formed using smooth roll calendering as the exclusive laminating step and comprising a film layer and a nonwoven layer wherein said nonwoven layer contains a pattern of bond areas and said film has a higher degree of attachment to said nonwoven in said bond areas which provides a laminate peel strength of at least 45 grams between said film and nonwoven layers and in the laminate said film has a generally uniform thickness.

2. The laminate of claim 1 wherein said film comprises an amorphous polymer having a density in the range of from about 0.85 g/cc to about 0.94 g/cc and a crystallinity of less than about 30% and is a bonding layer in face-to-face contact with said nonwoven.

3. The laminate of claim 2 wherein said nonwoven has a basis weight in the range of from about 10 gsm to about 50 gsm and said film has a thickness in the range of from about 10 microns to about 30 microns.

4. The laminate of claim 3 wherein said film contains a filler in the amount of about 40% to about 75% by weight and said laminate has a moisture vapor transmission rate of at least about 300 g/m$^2$/24 hours.

5. The laminate of claim 2 wherein said film is a multi-layer coextruded film.

6. The laminate of claim 3 wherein said film is a multi-layer coextruded film.

7. The laminate of claim 4 wherein said film is a multi-layer coextruded film.

8. The laminate of claim 4 wherein said filler comprises calcium carbonate.

9. The laminate of claim 7 wherein said filler comprises calcium carbonate.

10. The laminate of claim 9 wherein said moisture vapor transmission rate of said laminate is at least about 800 g/m$^2$/24 hours.

11. The laminate of claim 3 wherein the laminate has a hydrohead of at least 50 mbar.

12. The laminate of claim 5 wherein said film comprises a LLDPE layer and said amorphous layer comprises a single site catalyzed LLDPE with density less than about 0.89 g/cc.

13. The laminate of claim 12 wherein said single site catalyzed LLDPE layer also comprises an amorphous polyalphaolefin.

14. The laminate of claim 13 having a moisture vapor transmission rate of at least about 3000 g/m$^2$/24 hours and an abrasion resistance level of at least 3.

15. The laminate of claim 14 wherein said nonwoven comprises a propylene polymer spunbond and said laminate has a machine direction tensile of at least about 3000 g.

16. A medical fabric comprising the laminate of claim 7 and compliant under viral barrier tests.

17. A medical fabric comprising the laminate of claim 9 and compliant under viral barrier tests.

18. A medical fabric comprising the laminate of claim 14 and compliant under viral barrier tests.

19. The laminate of claim 2 wherein said amorphous bonding layer comprises between about 45% and about 75% by weight of a crystalline component.

20. A protective apparel selected from surgical gowns and surgical drapes comprising the medical fabric of claim 16.

21. A protective apparel selected from surgical gowns and surgical drapes comprising the medical fabric of claim 17.

22. A protective apparel selected from surgical gowns and surgical drapes comprising the medical fabric of claim 18.

23. The laminate of claim 2 wherein said nonwoven is unattached to said film between said pattern bond areas.

24. A personal care product comprising the laminate of claim 23.

* * * * *

UNITED STATES PATENT AND TRADEMARK OFFICE
CERTIFICATE OF CORRECTION

PATENT NO. : 6,238,767 B1
DATED : May 29, 2001
INVENTOR(S) : Ann L. McCormack et al.

It is certified that error appears in the above-identified patent and that said Letters Patent is hereby corrected as shown below:

<u>Column 5,</u>
Line 25, "1800" should read -- 180° --

Signed and Sealed this

Eleventh Day of June, 2002

Attest:

Attesting Officer

JAMES E. ROGAN
*Director of the United States Patent and Trademark Office*